United States Patent
Handzsuj et al.

(10) Patent No.: US 8,950,399 B2
(45) Date of Patent: Feb. 10, 2015

(54) METHOD FOR AUTOMATICALLY CONTROLLING A VENTILATION OR BREATHING SYSTEM AS WELL AS A CORRESPONDING VENTILATION OR BREATHING SYSTEM

(75) Inventors: Thomas Handzsuj, Lübeck (DE); Ernst Schubert, Lübeck (DE); Frank Ralfs, Lübeck (DE); Marcus Eger, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1528 days.

(21) Appl. No.: 12/264,980

(22) Filed: Nov. 5, 2008

(65) Prior Publication Data

US 2009/0114224 A1    May 7, 2009

(30) Foreign Application Priority Data

Nov. 7, 2007  (DE) .......................... 10 2007 052 897

(51) Int. Cl.
*A61M 16/00*   (2006.01)
*A61B 5/091*   (2006.01)

(52) U.S. Cl.
CPC ....... *A61M 16/0051* (2013.01); *A61M 16/0069* (2014.02); *A61B 5/091* (2013.01);
(Continued)

(58) Field of Classification Search
USPC ............. 128/200.24, 204.18, 204.13, 204.21, 128/204.26
See application file for complete search history.

(56) References Cited

U.S. PATENT DOCUMENTS 5,044,362 A * 9/1991 Younes .................... 128/204.21
5,107,830 A * 4/1992 Younes .................... 128/204.18

(Continued)

OTHER PUBLICATIONS

Ambrosino et al., Proportional assist ventilation (PAV): a significant advance or a futile struggle between logic and practice?, Thorax 2002, 57, pp. 272-276.

*Primary Examiner* — Loan H Thanh
*Assistant Examiner* — Sundhara Ganesan
(74) *Attorney, Agent, or Firm* — McGlew and Tuttle, P.C.

(57) ABSTRACT

A method is provided for automatically controlling a ventilation or breathing system with a ventilation unit (7), which is controlled by a control unit (5), in order to deliver an assist pressure preset by the control unit, wherein the current values of the tidal volume flow Flow(t) and those of the volume V(t) are detected in the control unit. The control unit (5) may carry out a proportionally assisting ventilation method (PAV: Proportional Assist Ventilation) by a factor for a degree of compensation (PPSp) being selected by the control unit and by the parameters for the volume assist (VA) and the flow assist (FA) being determined by:

$$VA = PPSp \cdot \Delta E$$

$$FA = PPSp \cdot \Delta R,$$

wherein $\Delta E$ is the deviation of a measured or assumed elastance ($E_{measured}$) of the patient from an ideal elastance ($E_{ideal}$) and $\Delta R$ is the deviation of a measured or assumed resistance ($R_{measured}$) of the patient from an ideal resistance ($R_{ideal}$). The assist pressure $PS(t) = VA \cdot V(t) + FA \cdot Flow(t)$ is determined from this by the control unit with the flow delivery device (ventilation unit (7)) being set such as to deliver this assist pressure.

29 Claims, 3 Drawing Sheets

(52) U.S. Cl.
CPC .................. *A61M2016/0027* (2013.01); *A61M 2016/0036* (2013.01); *A61M 2205/502* (2013.01); *A61M 2230/42* (2013.01); *A61M 2230/432* (2013.01); *A61M 2230/46* (2013.01)
USPC ............ 128/204.23; 128/204.18; 128/204.21; 128/204.26

(56) References Cited

U.S. PATENT DOCUMENTS

| | | | |
|---|---|---|---|
| 5,535,738 A * | 7/1996 | Estes et al. ............... | 128/204.23 |
| 5,540,222 A * | 7/1996 | Younes .................... | 128/205.18 |
| 5,884,622 A * | 3/1999 | Younes .................... | 128/204.21 |
| 6,439,229 B1 * | 8/2002 | Du et al. ................... | 128/204.23 |
| 6,758,216 B1 * | 7/2004 | Berthon-Jones et al. | 128/204.23 |
| 7,066,173 B2 * | 6/2006 | Banner et al. ............ | 128/204.23 |
| 7,077,132 B2 * | 7/2006 | Berthon-Jones ......... | 128/204.23 |
| 7,100,607 B2 * | 9/2006 | Zdrojkowski et al. ... | 128/204.18 |
| 8,160,817 B2 | 4/2012 | Ranieri et al. | |
| 2006/0249148 A1 * | 11/2006 | Younes .................... | 128/204.18 |
| 2006/0278223 A1 * | 12/2006 | Younes .................... | 128/204.23 |
| 2007/0151563 A1 * | 7/2007 | Ozaki et al. .............. | 128/204.23 |
| 2007/0272241 A1 * | 11/2007 | Sanborn et al. .......... | 128/204.23 |
| 2009/0221926 A1 * | 9/2009 | Younes ......................... | 600/529 |

* cited by examiner

| τ (s) | R [mbar/(l/s)] | E [mbar/l] |
|---|---|---|
| 0.05 | 3.00 | 60.00 |
| 0.10 | 3.00 | 30.00 |
| 0.15 | 3.00 | 20.00 |
| 0.20 | 3.52 | 17.61 |
| 0.25 | 4.05 | 16.18 |
| 0.30 | 4.57 | 15.23 |
| 0.35 | 5.09 | 14.55 |
| 0.40 | 5.61 | 14.03 |
| 0.45 | 6.14 | 13.64 |
| 0.50 | 6.66 | 13.32 |
| 0.55 | 7.18 | 13.06 |
| 0.60 | 7.70 | 12.84 |
| 0.65 | 8.23 | 12.66 |
| 0.70 | 8.75 | 12.50 |
| 0.75 | 9.38 | 12.50 |
| 0.80 | 10.00 | 12.50 |
| 0.85 | 10.63 | 12.50 |
| 0.90 | 11.25 | 12.50 |
| 0.95 | 11.88 | 12.50 |
| 1.00 | 12.50 | 12.50 |
| 1.05 | 13.13 | 12.50 |
| 1.10 | 13.75 | 12.50 |
| 1.15 | 14.38 | 12.50 |
| 1.20 | 15.00 | 12.50 |
| 2.25 | 15.63 | 12.50 |
| 1.30 | 16.25 | 12.50 |
| 1.35 | 16.88 | 12.50 |
| 1.40 | 17.50 | 12.50 |
| 1.45 | 18.13 | 12.50 |
| 1.50 | 18.75 | 12.50 |

METHOD FOR AUTOMATICALLY CONTROLLING A VENTILATION OR BREATHING SYSTEM AS WELL AS A CORRESPONDING VENTILATION OR BREATHING SYSTEM

CROSS REFERENCE TO RELATED APPLICATIONS

This application claims the benefit of priority under 35 U.S.C. §119 of German Patent Application DE 10 2007 052 897.5 filed Nov. 7, 2007, the entire contents of which are incorporated herein by reference.

FIELD OF THE INVENTION

The present invention pertains to a method for automatically controlling a ventilation or breathing system with a ventilation unit, which is controlled by a control unit such as to deliver a pressure assist preset by the control unit, wherein the current values of the tidal volume flow Flow(t) and those of the tidal volume V(t) are detected in the control unit.

BACKGROUND OF THE INVENTION

In such methods, the desired assist pressure ($PS_{desired}$) can either be preset and set by the operating staff or it can be automatically determined by an expert system implemented in a control unit according to preset dependencies on certain measured values. One example is sold under the name Smartcare® system of Dräger Medical AG & Co. KG, in which a value is supplied for the desired assist pressure $PS_{desired}$ on the basis of measured values of the ventilation or breathing rate, tidal volume and end-tidal $CO_2$ concentration according to preset and preprogrammed rules and algorithms.

Besides, proportionally assisting methods are known, in which the patient's spontaneous ventilation or breathing is assisted. The degree of assist can be set separately according to the resistive and elastic components. These methods are also known under the terms "proportional assist ventilation" (PAV) and "proportional pressure assist" (PPS). The volume flow (Flow(t)) and the tidal volume (V(t)) are detected in these methods. The degree of assist is then determined with coefficients VA (Volume Assist) and FA (Flow Assist), which are to be set by the user, from the above-mentioned two measured values by the entire assist pressure being calculated as VA·V(t)+FA·Flow(t). In the prior-art respirators, which operate according to this principle of proportional pressure assist, the coefficients for the support FA and VA must be entered by the operating staff separately (cf., e.g., Younes, M.: "Proportional Assist Ventilation" in: Tobin M. J., ed. "Principles and practice of mechanical ventilation," New York, McGraw-Hill, 1994, pages 349-369).

SUMMARY OF THE INVENTION

An object of the present invention is to provide a method for automatically controlling a ventilation or breathing system, which can be operated by the operating staff in a simple and reliable manner and provides an optimal pressure assist for the patient, and to provide a corresponding ventilation or breathing system.

According to the present invention, a method is provided for automatically controlling a ventilation or breathing system with a ventilation unit (including a gas delivery means), which is controlled by a control unit such as to deliver an assist pressure preset by the control unit at the patient feed. The current values of the tidal volume flow Flow(t) and those of the tidal volume V(t) are detected in the control unit. The control unit carries out a proportionally assisting ventilation method (PAV: Proportional Assist Ventilation) with a factor being selected by the control unit for a degree of compensation (PPSp) and with the parameters for the volume assist (VA) and for the flow assist (FA) being determined by:

$$VA = PPSp \cdot \Delta E$$

$$FA = PPSp \cdot \Delta R,$$

wherein $\Delta E$ is the deviation of a measured or assumed elastance ($E_{measured}$) of the patient from an ideal elastance ($E_{ideal}$) and $\Delta R$ is the deviation of a measured or assumed resistance ($R_{measured}$) of the patient from an ideal resistance ($R_{ideal}$), and by the assist pressure PS(t)=VA·V(t)+FA·Flow(t) being determined therefrom by the control unit and by the ventilation unit being set such as to deliver this assist pressure.

The assist pressure to be delivered is the pressure prevailing at the patient feed, e.g., at the Y-piece; it corresponds to the airway pressure during the inspiratory phase.

If it is described in connection with the present invention that the control unit is "prepared" for carrying out certain functions or method steps, this means that the control unit, which may also be composed of a plurality of subunits, is set up in terms of circuitry and programming to carry out the intended functions and steps. This preparation or setting up contains the presence of the electronic means suitable for the intended functions and steps (amplifiers, AD converters, signal method circuits, micromethods, etc.) and of data method means (methods and memories), which are connected to one another and prepared in terms of programming for carrying out the intended functions and method steps in the manner necessary for this, i.e., they are programmed with the specific programs such as to let the described functions and method steps be carried out by the control unit. The preparation of the control unit in terms of programming can, of course, also be divided among different subunits, e.g., a central computing unit, a fan control unit and a program module, which delivers output values from input data with a plurality of empirical rules programmed in advance (expert system). The transitions between the preparation in terms of circuitry and programming can be shifted in their embodiment, because preparation in terms of programming and data method functions may also be carried out by hardwired circuits. The design and implementation of the control unit for the defined functions can be readily embodied by experts.

In the method according to the present invention, a value for the desired assist pressure $PS_{desired}$ to be delivered by the ventilation or breathing system is preferably entered at a user interface of the control unit or it is determined by an expert system implemented in the control unit according to preset dependencies on the basis of measured values for the tidal volume, ventilation or breathing rate and end-tidal $CO_2$ concentration (et$CO_2$). The control unit is then prepared to determine, on the basis of an implemented controller function, after the end of at least one breathing cycle, a new value for the degree of compensation $PPSp_{new}$ from the previous value PPSp and the set point $PS_{desired}$ in such a way that the representative assist pressure <PS>, which is determined as a mean value determined over time, as a weighted mean value, as a median or as a maximum of the time curve of PS(t) during inspiration over one breathing cycle or over a plurality of breathing cycles, will reach the value $PS_{desired}$ within a plurality of breathing cycles exactly or on an average over a plurality of breathing cycles. A new value for the degree of compensation $PPSp_{new}$ is determined especially preferably from the previous value PPSp according to $PPSp_{new}=PPSp+(PS_{desired}-\langle PS\rangle)/V_{PPS}$, wherein the amplification $V_{PPS}$ is an indicator of the change in the representative assist pressure $\langle PS\rangle$ in relation to the change of PPSp, which is determined over a breathing cycle or a plurality of consecutive breathing cycles.

PPSp can consequently be adjusted continuously by means of a breath-based regulation such that a representative value of the assist pressure that becomes established corresponds, on average, to the desired assist pressure $PS_{desired}$ during the inspiration phase (e.g., the mean inspiratory pressure) over a plurality of breaths.

In a proportionally assisting method, a possible approach to assist is to compensate the patient's resistance and elastance such that circumstances as they occur in a healthy lung will become established. This is achieved by setting the values for the flow assist FA and the volume assist VA corresponding to the difference between the actual and ideal lung mechanics. According to the present invention, this compensation can also take place partially by the difference between the actual and ideal lung mechanics being corrected only partially, specified by a factor for the degree of compensation PPSp, a value of 1 for PPSp meaning 100% compensation towards the ideal lung mechanics and a PPSp of 0 means no compensation. The degree of compensation is usually between 0 and 1 (1 means full compensation, 0 no compensation), but it may also become greater than 1 when compensation is necessary beyond the ideal lung mechanics or when the real values of elastance and resistance exceed the assumed or measured values.

In the sense of the present invention, the lung mechanics ($R_{measured}$ and $E_{measured}$) can be determined by a measurement, on the one hand, and, on the other hand, by an estimation, which means a reduction to various types of lung mechanics in the simplest case. For example, the division into the following three types with different ratios of resistance and elastance is meaningful, because it covers the clinically occurring cases of pathological lung mechanics in a suitable manner:

Restrictive(hypothesis:$E_{measured}$=30 mbar/L, $R_{measured}$=3 mbar/(L/sec))     1

Obstructive(hypothesis:$E_{measured}$=12.5 mbar/L, $R_{measured}$=15 mbar/(L/sec))     2

Restrictive & obstructive(hypothesis:$E_{measured}$=30 mbar/L,$R_{measured}$=15 mbar/(L/sec)).     3

The type may be preset directly by the user or set by an algorithm or set. Such an algorithm could also generate a warning for the case in which the set type presumably does not correspond to the real ratios any longer. A possible algorithm consists of the analysis of the respiratory time constant, which can be obtained, e.g., from passive phases of expiration (cf. Brunner et al., "Simple method to measure total expiratory time constant based on the passive expiratory flow-vs.-volume curve," *Critical Care Medicine*, 23(6): 1117-1122, June 1995; Morris et al., "Analysis of expiratory tidal flow patterns as a diagnostic tool in airflow obstruction," *Eur Respir J*, 1998; 12: 1113-1117). The term "time constant" is defined in connection with this application as the time constant of the idealized respiratory system of the patient. It characterizes the time characteristic of the state variables (pressure, flow, volume) of a linear model of the respiratory system, which can be described by only two parameters, resistance and elastance. The numerical value of the time constant is identical to the time that is needed to passively expire 63% of the volume inspired previously.

If the time constant is known, meaningful values for resistance and elastance can be determined under the assumption of a preset dependence of resistance and elastance on the time constant. Any deviations of these resulting assumed values from the real values of lung mechanics are hardly relevant in the control of ventilation or breathing, because ventilation or breathing is based predominantly on the hypothetical values of resistance and elastance in connection with the present invention.

The clinically substantiated assumption that patients with a low time constant are characterized mainly by normal resistance and increased elastance (e.g., in case of acute pulmonary failure), while patients with a high time constant have normal elastance and increased resistance (e.g., in chronic obstructive diseases) is used to preset the dependence of resistance and elastance on the time constant.

The range of physiologically meaningful time constants is divided into three parts in the following exemplary embodiment (see FIG. 1). An ideal resistance ($R_{measured}$=3 mbar/(L/sec)) is assumed for τ<0.2 sec and an ideal elastance ($E_{measured}$=12.5 mbar/(L/sec)) is assumed for τ>0.65 sec. The resistance is linearly interpolated for the part located between these limits. Thus, the exemplary embodiment supplies a corresponding hypothetical value of resistance and elastance for each time constant (e.g., a time constant determined by measurement). Other hypothetical dependencies between resistance and the time constant and between elastance and the time constant are also conceivable according to the present invention. The resistance and elastance values resulting from such a dependence can be used either directly for automatic ventilation or breathing assist or as a plausibility check in case of manual presetting of the type of the patient's lung mechanics (obstructive, restrictive, obstructive & restrictive).

The procedure of ventilation or breathing assist shall be explained on the basis of the following numerical example, in which ideal lung mechanics with an ideal elastance of $E_{ideal}$=12.5 mbar/L and an ideal resistance of $R_{ideal}$=3 mbar/(L/sec) is assumed:

Patient's measured lung mechanics:$E_{measured}$=30 mbar/L,$R_{measured}$=10 mbar/(L/sec)

Deviation from the ideal lung mechanics:

ΔE=(30−12.5)mbar/L=17.5 mbar/L

ΔR=(10−3)mbar/(L/sec)=7 mbar/(L/sec)

PPS$p$=0.8(selected degree of compensation)

Proportional assist factors:

VA=0.8×17.5 mbar/L=14 mbar/L

FA=0.8×7 mbar/(L/sec)=5.6 mbar/(L/sec).

The ideal lung mechanics can also be assumed with an elastance $E_{ideal}$ of 0 and a resistance of $R_{ideal}$ of 0, which is especially meaningful when disturbed ventilation or breathing drive is present in the patient. The following is thus obtained for the above example:

Patient's lung mechanics:$E_{measured}$=30 mbar/L, $RE_{measured}$=10 mbar/(L/sec)

Deviation from the ideal lung mechanics:

$\Delta E = 30$ mbar/L $\Delta R = 10$ mbar/(L/sec)

PPS$p$=0.8(selected degree of compensation)

Proportional assist factors:

VA=0.8×30 mbar/L=24 mbar/L

FA=0.8×10 mbar/(L/sec)=8 mbar/(L/sec).

When the present invention is used, it is preferred to adapt the degree of compensation interactively in the manner of a regulator such that the above-described pressure set point PS$_{desired}$ will be reached exactly or as an average over several breathing cycles. This can happen, e.g., such that a new or next degree of compensation is determined after one or more breathing cycles according to the formula:

PPS$p_{new}$=PPS$p$+(PS$_{desired}$−<PS>)/V$_{PPS}$, where the amplification V$_{PPS}$ is an indicator of the change of the assist pressure <PS> that becomes established in relation to the change of PPSp, which is determined over a breathing cycle or a plurality of consecutive breathing cycles. Here, <PS> designates a representative value of the time curve of PS(t), which can be determined, e.g., as a mean value averaged over time, as a weighted mean, as a median or as a maximum of the time curve of PS(t) during inspiration over one breathing cycle or over a plurality of breathing cycles.

The amplification may be, e.g., a linear function of the ratio of the changes: V$_{PPS}$=Δ<PS>/ΔPPSp. As an alternative, the amplification can be determined, e.g., from an exponential relationship:

$V_{PPS} = \Delta(PS)/(e^{k \cdot \Delta PPSp} - 1)$ in which, e.g., k=1.823, which causes that in case of a ΔPPSp of 0.1, the amplification V$_{PPS}$ is reduced by half compared to the linear hypothesis. An example for the calculation of a new value PPSp is shown, e.g., by the following numerical values:

Set point of assist pressure $PS_{desired}$=15 mbar

Actual value of assist pressure:<$PS$>=13 mbar at PPS$p$ 0.60.

Previous assist pressure:<$PS$>$_{alt}$=11 mbar at PPS$p$ 0.50.

Hypothesis: linear dependence for determining V$_{PPS}$ $V_{PS}$=(13 mbar−11 mbar)/(0.60−0.50)=20 mbar PPS$p_{new}$=PPS$p$+(PS$_{desired}$−<PS>)/V$_{PPS}$=0.60+0.10=0.70

This calculation corresponds to a deadbeat regulator. Also meaningful is the realization of a "half-deadbeat regulator," in which PPSp is changed only corresponding to half or another portion of the deviation, i.e., PPSp$_{new}$=0.65 here. The value of PPSp$_{new}$ is recalculated after the end of one or more breathing cycles and then maintained at a constant level until the recalculation.

V$_{PPS}$ depends on the current lung mechanics and the current spontaneous breathing effort. The unlimited (calculated) value is used for the calculation of the current amplification even in case of a limitation of the assist pressure as well. Since no further assistance takes place in this case, lower values are obtained for V$_{PPS}$. As a consequence, this leads to a faster decline of PPSp.

The change in PPSp, i.e., the calculation of PPSp$_{new}$ and the takeover of this new value as the current value for PPSp, can take place over each breath, but also over several breaths, just as the PPSp amplification can be determined from one breath or averaged over a plurality of breaths. Since the amplification V$_{PPS}$ is undetermined at the beginning, it is necessary to start with a meaningful start value for PPSp in the first step (e.g., PPSp=0.50) and a change with fixed value (e.g., 0.10) with the correct sign must be used in the second step.

If no measured values are available for the lung mechanics, the following start values are assumed for a patient who is estimated as being "obstructive:"

$E_{measured}$=12.5 mbar/L,$R_{measured}$=15 mbar/(L/sec)

PPSp=0.50

Deviations from the ideal lung mechanics:

$\Delta E = 0$ $\Delta R = 12$ mbar/(L/sec)

Resulting assist factors:

VA=0

FA=0.5×12 mbar/(L/sec)=6 mbar/(L/sec)

The adaptation of PPSp by the regulator would lead to overcompensation ("runaway") in a patient with normal lung mechanics but excessively weak ventilation or breathing drive. The assist pressure value or assist pressure course is therefore limited to a pressure value that is related to the desired assist pressure and the respirator is caused to behave as in classical assisted ventilation or breathing in this borderline case. The pressure limit value can be selected, e.g., proportionally to the desired assist pressure or additively thereto.

Concerning the possibility of measuring the elastance E and resistance R, reference is made, e.g., to the applicant's dependent application EP 07005690 (corresponding to U.S. Pat. No. 8,160,817).

The present invention will be explained in more detail below on the basis of an exemplary embodiment with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
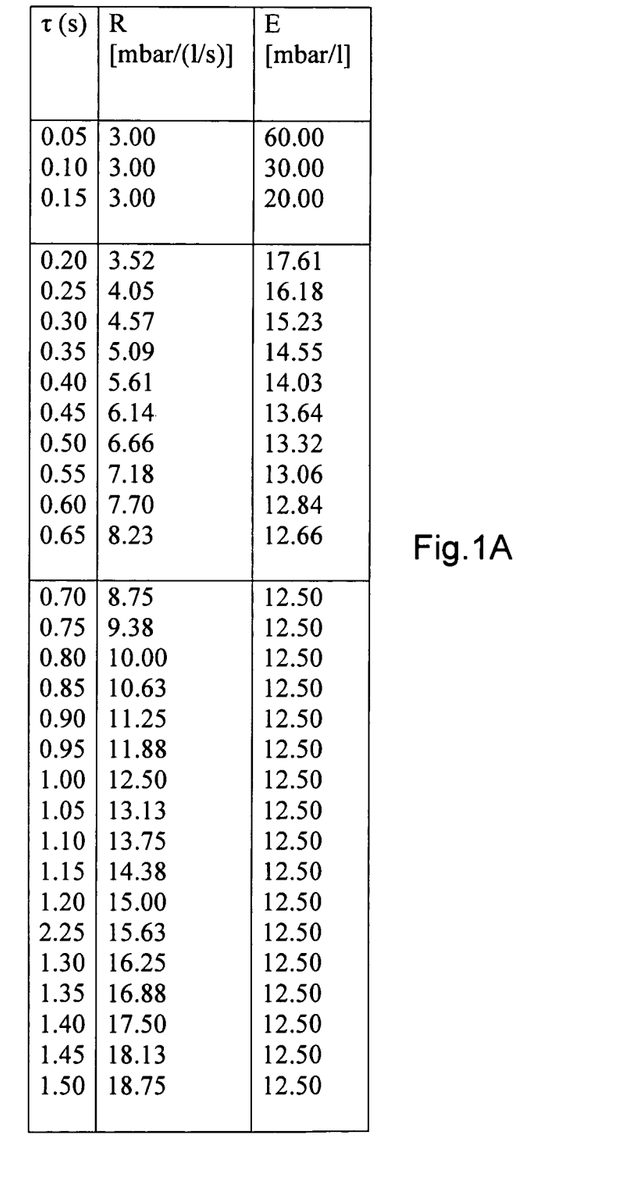
FIG. 1A is an exemplary table for a predetermined standard or typical dependence between elastance, on the one hand, and resistance, on the other hand, and the time constant.
Figure 1B:
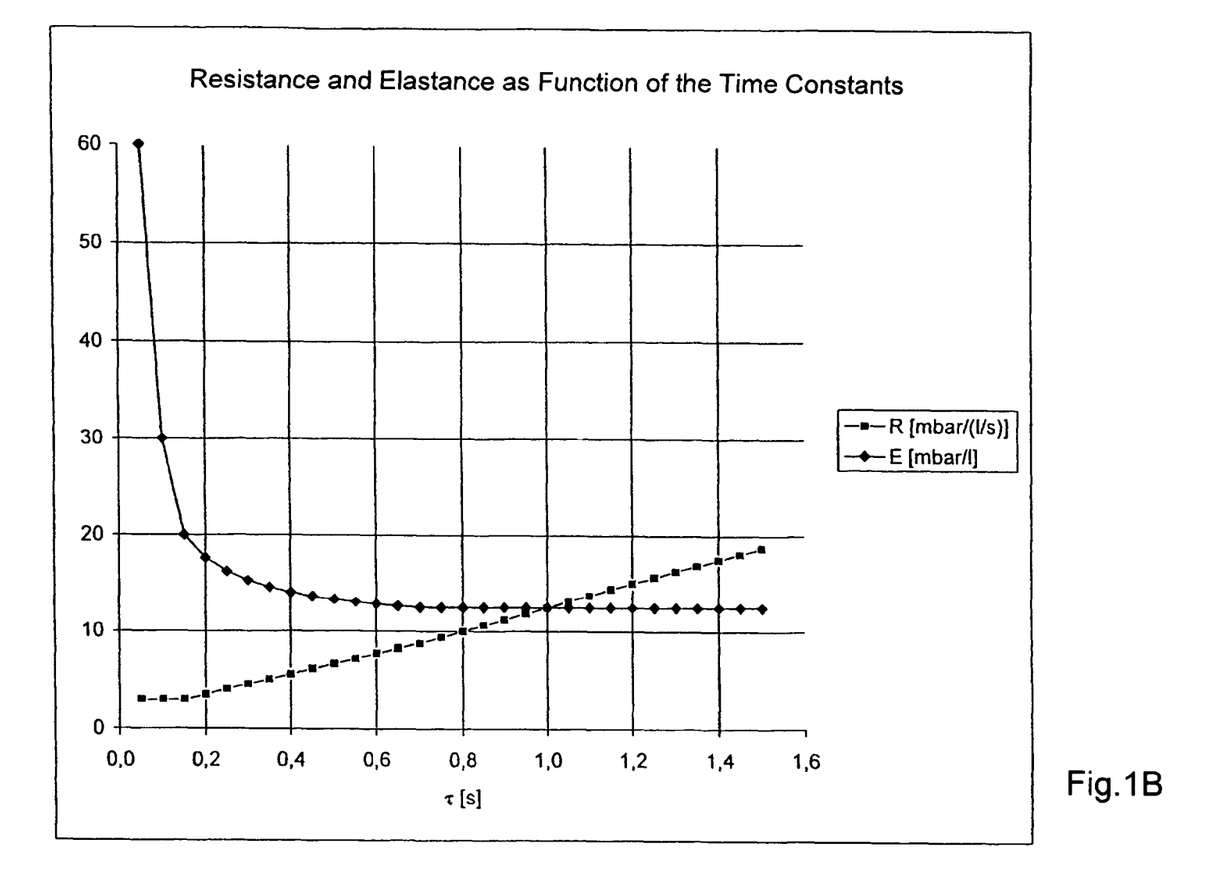
FIG. 1B is a graph for the predetermined standard or typical dependence between elastance, on the one hand, and resistance, on the other hand, and the time constant.

Referring to the drawings in particular, in one exemplary embodiment, FIG. 1A shows a table, in which the left-hand column shows the range of the physiologically meaningful time constants and the middle and right-hand columns show the predetermined (e.g., empirical) standard dependencies of elastance and resistance on the time constant. The range of the meaningful time constants is divided according to the predetermined standard dependencies into three parts. Ideal resistance ($R_{measured}$=3 mbar/(L/sec)) is assumed for $\tau$<0.2 sec and ideal elastance ($E_{measured}$=12.5 mbar/(L/sec)) is assumed for $\tau$>0.65 sec. The resistance is interpolated linear for the part located between these limits. Thus, the exemplary embodiment yields a corresponding hypothetical value of the resistance and elastance for each time constant. The graphics visualize the dependence selected in the table between resistance, on the hand, and elastance, on the other hand, and the time constant. Conversely, FIGS. 1A and 1B make it clear that from a dependence of elastance and resistance determined in advance, as is shown in FIGS. 1A and 1B, the determination of the time constant makes it possible to obtain values $E_{measured}$ and $R_{measured}$ by converting the graphically represented functions.

Figure 2:
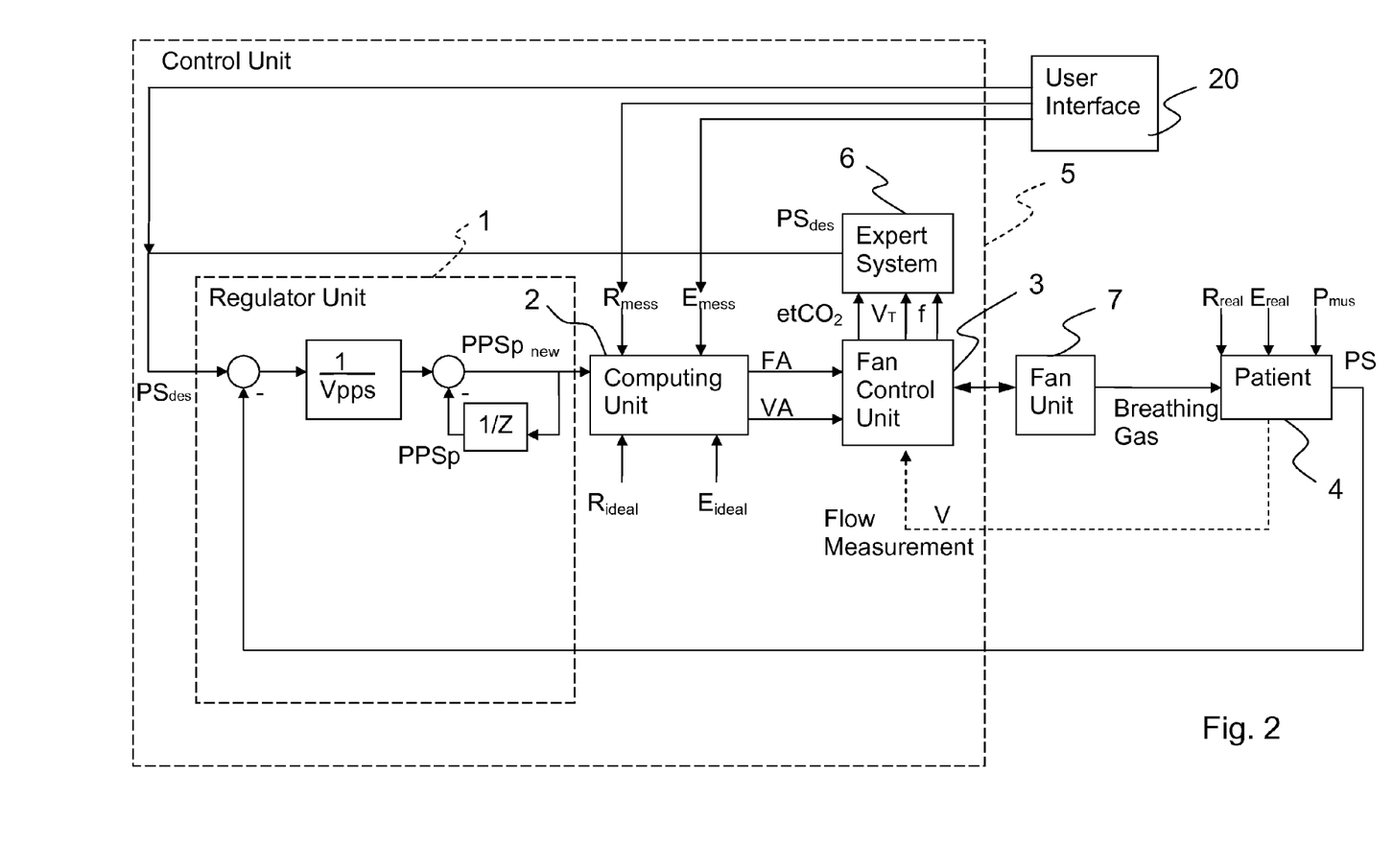
FIG. 2 is a block diagram of a control circuit, with which the method according to the present invention for controlling the ventilation or breathing system can be carried out.

FIG. 2 illustrates a control circuit for carrying out the method according to the present invention for controlling a ventilation or breathing system based on a control unit 5 and a ventilation unit (gas delivery device/fan unit) 7. An expert system 6 is contained in the control unit 5 in this exemplary embodiment. The expert system yields a set point for the assist pressure $PS_{desired}$ on the basis of measured values of the end-tidal $CO_2$ value, the tidal volume $V_T$ and the ventilation or breathing rate f, which is sent by a fan control means 3. A value for the desired assist pressure $PS_{desired}$ to be delivered by the ventilation or breathing system may also be entered at a user interface 20 of the control unit 5.

The regulator unit 1 present in the control unit delivers a new value for the degree of compensation $PPSp_{new}$ from the current representative assist pressure <PS> and the desired assist pressure $PS_{desired}$. The deviation <PS>−$PS_{desired}$ is divided for this by the amplification factor $V_{PPS}$ and added as an increment to the old value of PPSp. The current flow assist FA and the volume assist VA are calculated in the computing unit 2 from $PPSp_{new}$, the hypothetical or measured parameters of the lung mechanics ($R_{measured}$, $E_{measured}$) as well as the corresponding ideal values ($R_{ideal}$, $E_{ideal}$). The fan control means 3 connected to the patient's lung operates in ventilation or breathing mode "PPS" or "PAV" and uses the calculated values for FA and VA as well as of the measured volume flow Flow(t) and of the tidal volume V(t) in order to calculate from this the current value of the assist pressure according to PS(t)=VA·V(t)+FA·Flow(t). The ventilation unit 7 is then set according to this assist pressure PS(t) in order to deliver this assist pressure to the patient 4.

Measurement of the flow into the patient's lung 4, which is commonly performed for intensive care respirators, is necessary for this. The actual mechanical breathing characteristics of the patient's lungs are described by the parameters $R_{real}$ and $E_{real}$. The muscle pressure of the respiratory muscles $P_{mus}$ reflects the patient's respiratory efforts, to which the respirator responds by pressure assist on the basis of the flow measurement.

While specific embodiments of the invention have been shown and described in detail to illustrate the application of the principles of the invention, it will be understood that the invention may be embodied otherwise without departing from such principles.

What is claimed is:

1. A method for automatically controlling a ventilation or breathing system, the method comprising the steps of:

providing a ventilation or breathing system with a ventilation unit controlled by a control unit for delivery of an assist pressure preset by said control unit;

detecting current values of the tidal volume flow (Flow(t)) and of the volume (V(t)) and providing the detected values to said control unit;

carrying out a proportionally supporting ventilation method (PAV: Proportional Assist Ventilation) with the control unit with a factor for a degree of compensation (PPSp) being selected by the control unit and by the parameters for the volume assist (VA) and the flow assist (FA) being determined by:

$$VA = PPSp \cdot \Delta E$$

$$FA = PPSp \cdot \Delta R,$$

wherein $\Delta E$ is the deviation of a measured or assumed elastance ($E_{measured}$) of the patient from an ideal elastance ($E_{ideal}$) and $\Delta R$ is the deviation of a measured or assumed resistance ($R_{measured}$) of the patient from an ideal resistance ($R_{ideal}$);

using an assist pressure (PS(t)) determined by the control unit from VA and FA wherein PS(t)=VA·V(t)+FA·Flow(t) is determined to set the ventilation unit such as to deliver this assist pressure;

providing an input of a value for a desired assist pressure ($PS_{desired}$) to be delivered by the ventilation or breathing system, wherein said control unit:

calculates a representative assist pressure <PS>, which is determined as a mean over time, as a weighted mean, as a median or as a maximum of the time curve of PS(t) during the inspiration over one breathing cycle or over a plurality of breathing cycles; and determines a new value for the degree of compensation $PPSp_{new}$ from the previous value of PPSp according to $PPSp_{new}$=PPSp+($PS_{desired}$−<PS>)/$V_{PPS}$, wherein the amplification $V_{PPS}$ is an indicator of the change of the representative assist pressure <PS> in relation to the change of PPSp, which indicator is determined over one breathing cycle or over a plurality of consecutive breathing cycles, wherein:

said control unit determines the value for the amplification $V_{PPS}$ as a ratio of the change in the representative assist pressure <PS> to the change of the parameter PPSp over one or more consecutive breathing cycles according to at least one of the formula:

$$V_{PPS} = \Delta <PS>/\Delta PPSp; \text{ and}$$

$$V_{PPS} = \Delta <PS>/(e^{k \cdot \Delta PPSp} - 1),$$

wherein k is a constant and wherein the assist pressure PS(t) is limited to a pressure limit value that is related to the desired assist pressure $PS_{desired}$.

2. A method in accordance with claim 1, wherein a value from the range of 0 to 15 mbar/L is assumed and used for the ideal elastance ($E_{ideal}$) and a value ranging from 0 to 5 mbar/(L/sec) is assumed and used for the ideal resistance ($R_{ideal}$).

3. A method in accordance with claim 1, further comprising:

measuring airway pressure ($p_{aw}$(t));

calculating with the control unit the resistance ($R_{measured}$) and elastance ($E_{measured}$) on the basis of the measured values for the airway pressure $p_{aw}$(t) and the tidal volume flow (Flow(t)).

4. A method in accordance with claim 1, wherein values for the resistance ($R_{measured}$) and elastance ($E_{measured}$) of the patient are entered as numerical values at the user interface.

5. A method in accordance with claim 1, wherein pairs of values for the resistance ($R_{measured}$) and elastance ($E_{measured}$) are selected from a plurality of preset typified value pairs.

6. A method in accordance with claim 1, wherein said control unit automatically proposes values for the resistance ($R_{proposed}$) and elastance ($E_{proposed}$) of the patient on the basis of a determination of the time constant of the breathing mechanics ($\tau_{regress}$) and of predetermined and stored standard dependencies of the resistance and elastance, respectively, on the time constant, wherein $\tau_{regress}$ is obtained by means of linear regression of the flow-vs.-volume curve during a passive expiration phase.

7. A method in accordance with claim 6, wherein the predetermined and stored standard dependencies make provisions for dividing the range of physiologically meaningful time constants into three parts, wherein two part limits ($\sigma_1$ and $\tau_2$) are defined as $\tau_1 < \tau_2$, and an ideal resistance is assumed for $\tau_{regress} < \tau_1$ and an ideal elastance is assumed for $\tau_{regress} > \tau_2$, and the resistance is interpolated linearly for the part located between these limits.

8. A method in accordance with claim 6, wherein the values for the resistance ($R_{measured}$) and elastance ($E_{measured}$) of the patient are equated with the corresponding proposed values for the resistance ($R_{proposed}$) and elastance ($E_{proposed}$).

9. A method in accordance with claim 6, wherein said control unit compares proposed values for resistance ($R_{proposed}$) and elastance ($E_{proposed}$) with resistance ($R_{measured}$) and elastance ($E_{measured}$) values assumed or determined by one of:
measuring airway pressure ($p_{aw}(t)$) and calculating with the control unit the resistance ($R_{measured}$) and elastance ($E_{measured}$) on the basis of the measured values for the airway pressure $p_{aw}(t)$ and the tidal volume flow (Flow(t));
entering values for the resistance ($R_{measured}$) and elastance ($E_{measured}$) of the patient as numerical values at the user interface; and
selecting pairs of values for the resistance ($R_{measured}$) and elastance ($E_{measured}$) at the user interface from a plurality of preset typified value pairs whereby an indication is provided when the deviations between ($R_{proposed}$) and ($R_{measured}$) or between ($E_{proposed}$) and ($E_{measured}$) exceed a preset threshold.

10. A method in accordance with claim 1, further comprising:
providing resistance ($R_{measured}$) and elastance ($E_{measured}$) values assumed or determined by one of: measuring airway pressure ($p_{aw}(t)$) and calculating with the control unit the resistance ($R_{measured}$) and elastance ($E_{measured}$) on the basis of the measured values for the airway pressure $p_{aw}(t)$ and the tidal volume flow (Flow(t)); entering values for the resistance ($R_{measured}$) and elastance ($E_{measured}$) of the patient as numerical values at the user interface; and selecting pairs of values for the resistance ($R_{measured}$) and elastance ($E_{measured}$) at the user interface from a plurality of preset typified value pairs;
determining, with the control unit, a ratio $R_{measured}/E_{measured}$ from the assumed or determined values for resistance ($R_{measured}$) and elastance ($E_{measured}$);
comparing an indicator for the time constant ($\tau_{R/E}$), where $\tau_{R/E} = R_{measured}/E_{measured}$, to an indicator obtained for the regression time constant ($\tau_{regress}$) obtained from a linear regression of the flow-vs.-volume curve during a passive expiration phase and to yield an indication when the deviation between $\tau_{R/E}$ and $\tau_{regress}$ exceeds a preset threshold.

11. A method in accordance with claim 1, wherein a minimum duration of the pressure rise at the beginning of inspiration, is entered via the user interface of said control unit.

12. A method in accordance with claim 1, wherein the pressure limit value is selected in proportion to the desired assist pressure $PS_{desired}$ or additively thereto.

13. A ventilation or breathing system for automatically controlled ventilation or breathing, the ventilation or breathing system comprising:
a ventilation unit for delivering an assist pressure;
a control unit detecting current values of the tidal volume, flow (Flow(t)) and volume (V(t)) and receiving and storing assumed or measured values for a resistance ($R_{measured}$) and an elastance ($E_{measured}$) of the patient as well as for an ideal resistance ($R_{ideal}$) and an ideal elastance ($E_{ideal}$) and receiving an input of a value for an initial desired assist pressure ($PS_{desired}$) to be delivered by the ventilation or breathing system, wherein said control unit carries out a proportionally assisting ventilation method (PAV: Proportional Assist Ventilation) by a factor for a degree of compensation (PPSp) selected in said control unit and by parameters for the volume assist (VA) and the flow assist (FA) being determined by said control unit according to:

$$VA = PPSp \cdot \Delta E$$

$$FA = PPSp \cdot \Delta R$$

wherein $\Delta E$ is the deviation of the measured or assumed elastance ($E_{measured}$) of the patient from the ideal elastance $E_{ideal}$ and $\Delta R$ is the deviation of a measured or assumed resistance ($R_{measured}$) of the patient from an ideal resistance ($R_{ideal}$), and by the assist pressure $PS(t) = VA \cdot V(t) + FA \cdot Flow(t)$ being determined from this, and controlling said ventilation unit to deliver said assist pressure, wherein said control unit at least one of:
determines a new value for the degree of compensation ($PPSp_{new}$) from the previous value PPSp and determines $PS_{desired}$ on the basis of an implemented control function after the end of at least one breathing cycle in such a way that a representative assist pressure (<PS>), which is determined as a mean over time, as a weighted mean, as a median or as a maximum of the time curve of PS(t) during inspiration over one breathing cycle or over a plurality of breathing cycles, is reached exactly or as an average over several breathing cycles; and
calculates a representative assist pressure (<PS>), which is determined as a mean value over time, as a weighted mean, as a median or as a maximum of the time curve of PS(t) during the inspiration over one breathing cycle or over a plurality of breathing cycles, and determines a new value for the degree of compensation ($PPSp_{new}$) from the previous value of PPSp according to $PPSp_{new} = PPSp + (PS_{desired} - <PS>)/V_{PPS}$, wherein the amplification $V_{PPS}$ is an indicator of the change in <PS> in relation to the change in PPSp, which indicator is determined over one breathing cycle or over a plurality of consecutive breathing cycles.

14. A ventilation or breathing system in accordance with claim 13, wherein said control unit determines $V_{PPS}$ as a ratio of the change in the representative assist pressure (<$P_S$>) to the change in the parameter PPSp over one or more consecutive breathing cycles according to the formula: $V_{PPS} = \Delta <PS>/\Delta PPSp$.

15. A ventilation or breathing system in accordance with claim 13, wherein said control unit determines $V_{PPS}$ as a ratio of the change in the representative assist pressure (<$P_S$>) to the change in the parameter PPSp over one or more consecutive breathing cycles according to the formula $V_{PPS}=\Delta(PS)/(e^{k \cdot PPSp}-1)$, wherein k is a constant.

16. A ventilation or breathing system in accordance with claim 13, further comprising measuring means for measuring the airway pressure ($P_{aw}(t)$), wherein said control unit is prepared to calculate the resistance ($R_{measured}$) and elastance ($E_{measured}$) on the basis of the measured values for the airway pressure ($p_{aw}(t)$) and the tidal volume flow (Flow(t)).

17. A ventilation or breathing system in accordance with claim 16, wherein said control unit determines a ratio $R_{measured}/E_{measured}$ from a hypothetical or determined values for the resistance $R_{measured}$ and elastance $E_{measured}$ and compares this indicator for the time constant $\tau_{R/E}=R_{measured}/E_{measured}$ to the indicator obtained for the time constant $\tau_{regress}$ obtained from a linear regression of the flow-vs.-volume curve during a passive expiration phase and to send an indication when the deviation between $\tau_{R/E}$ and $\tau_{regress}$ exceeds a preset threshold.

18. A ventilation or breathing system in accordance with claim 13, wherein the user interface is for selecting values for the resistance ($R_{measured}$) and elastance ($E_{measured}$) from a plurality of preset typified combinations of values for ($E_{measured}$) and ($R_{measured}$).

19. A ventilation or breathing system in accordance with claim 18, wherein said control unit determines a ratio $R_{measured}/E_{measured}$ from a hypothetical value or determined values for the resistance ($R_{measured}$) and elastance ($E_{measured}$) and compares this indicator for the time constant $\tau_{R/E}=R_{measured}/E_{measured}$ to the indicator obtained for the time constant $\tau_{regress}$ obtained from a linear regression of the flow-vs.-volume curve during a passive expiration phase and to send an indication when the deviation between $\tau_{R/E}$ and $\tau_{regress}$ exceeds a preset threshold.

20. A ventilation or breathing system in accordance with claim 13, wherein the control unit proposes or presents automatic values for the resistance ($R_{proposed}$) and elastance ($E_{proposed}$) of the patient on the basis of a determination of the time constant of the mechanics of breathing ($\tau_{regress}$) and predetermined and stored standard dependencies of the elastance, on the one hand, and of the resistance, on the other hand, on the time constant, wherein the time constant ($\tau_{regress}$) is obtained by means of linear regression of the flow-vs.-volume curve during a passive expiration phase.

21. A ventilation or breathing system in accordance with claim 20, wherein said control unit is prepared such that the predetermined and stored standard dependencies of the elastance, on the one hand, and of the resistance, on the other hand, on the time constant make provisions for dividing the range of physiologically meaningful time constants into three parts, wherein two part limits, namely, $\tau_1$ and $\tau_2$, are defined by $\tau_1<\tau_2$, and an ideal resistance is assumed for $\tau_{regress}<\tau_1$ and an ideal elastance is assumed for $\tau_{regress}>\tau_2$, and the resistance is interpolated linearly for the part located between these limits.

22. A ventilation or breathing system in accordance with claim 21, wherein said control unit compares proposed values for the resistance ($R_{proposed}$) and elastance ($E_{proposed}$) with the values assumed or determined by one of: measuring means for measuring the airway pressure ($P_{aw}(t)$), and the user interface is for selecting values for the resistance ($R_{measured}$) and elastance ($E_{measured}$) from a plurality of preset typified combinations of values for ($E_{measured}$) and ($R_{measured}$), said control unit sending an indication when the deviations between ($R_{proposed}$) and ($R_{measured}$) or between ($E_{proposed}$) and ($E_{measured}$) exceed a preset threshold.

23. A ventilation or breathing system in accordance with claim 20, wherein said control unit is prepared such that the values for the resistance ($R_{proposed}$) and elastance ($E_{measured}$) of the patient are equated with the corresponding proposed values for the resistance ($R_{proposed}$) and elastance ($E_{proposed}$).

24. A ventilation or breathing system in accordance with claim 20, wherein said control unit compares proposed values for the resistance ($R_{proposed}$) and elastance ($E_{proposed}$) with the values assumed or determined by one of: measuring means for measuring the airway pressure ($P_{aw}(t)$), and the user interface is for selecting values for the resistance ($R_{measured}$) and elastance ($E_{measured}$) from a plurality of preset typified combinations of values for ($E_{measured}$) and ($R_{measured}$), said control unit sending an indication when the deviations between ($R_{proposed}$) and ($R_{measured}$) or between $E_{proposed}$ and ($E_{measured}$) exceed a preset threshold.

25. A ventilation or breathing system in accordance with claim 13, wherein said user interface sets a minimum duration of the pressure rise at the beginning of inspiration.

26. A ventilation or breathing system in accordance with claim 13, wherein said control unit limits the assist pressure (PS(t)) to a pressure value that is related to a desired assist pressure ($PS_{desired}$).

27. A ventilation or breathing system in accordance with claim 13, wherein said control unit limits the assist pressure (PS(t)) to a pressure value that is related to a desired assist pressure ($PS_{desired}$).

28. A method for automatically controlling a ventilation or breathing system, the method comprising the steps of:
providing a ventilation or breathing system with a ventilation unit controlled by a control unit for delivery of an assist pressure preset by said control unit;
detecting current values of the tidal volume flow (Flow(t)) and of the volume (V(t)) and providing the detected values to said control unit;
carrying out a proportionally supporting ventilation method (PAV: Proportional Assist Ventilation) with the control unit with a factor for a degree of compensation (PPSp) being selected by the control unit and by the parameters for the volume assist (VA) and the flow assist (FA) being determined by:

$$VA=PPSp \cdot \Delta E$$

$$FA=PPSp \cdot \Delta R,$$

wherein $\Delta E$ is the deviation of a measured or assumed elastance ($E_{measured}$) of the patient from an ideal elastance ($E_{ideal}$) and $\Delta R$ is the deviation of a measured or assumed resistance ($R_{measured}$) of the patient from an ideal resistance ($R_{ideal}$);
using an assist pressure (PS(t)) determined by the control unit from VA and FA wherein PS(t)=VA·V(t)+FA·Flow(t) is determined to set the ventilation unit such as to deliver this assist pressure;
providing an input of a value for a desired assist pressure ($PS_{desired}$) to be delivered by the ventilation or breathing system, wherein said control unit:
calculates a representative assist pressure <PS>, which is determined as a mean over time, as a weighted mean, as a median or as a maximum of the time curve of PS(t) during the inspiration over one breathing cycle or over a plurality of breathing cycles; and
determines a new value for the degree of compensation $PPSp_{new}$ from the previous value of PPSp according to $PPSp_{new}=PPSp+(PS_{desired}-<PS>)/V_{PPS}$, wherein the amplification $V_{PPS}$ is an indicator of the change of the representative assist pressure <PS> in relation to the change of PPSp, which indicator is determined over one breathing cycle or over a plurality of consecutive breathing cycles, wherein:

said control unit determines the value for the amplification $V_{PPS}$ as a ratio of the change in the representative assist pressure <PS> to the change of the parameter PPSp over one or more consecutive breathing cycles according to at least one of the formula:

$$V_{PPS} = \Delta<PS>/\Delta PPSp; \text{ and}$$

$$V_{PPS} = \Delta<PS>/(e^{k \cdot \Delta PPSp} - 1),$$

wherein k is a constant, wherein a value from the range of 0 to 15 mbar/L is assumed and used for the ideal elastance ($E_{ideal}$) and a value ranging from 0 to 5 mbar/(L/sec) is assumed and used for the ideal resistance ($R_{ideal}$).

29. A ventilation or breathing system in accordance with claim 13 wherein a value from the range of 0 to 15 mbar/L is assumed and used for the ideal elastance ($E_{ideal}$) and a value ranging from 0 to 5 mbar/(L/sec) is assumed and used for the ideal resistance ($R_{ideal}$).

\* \* \* \* \*